(12) United States Patent
Sato

(10) Patent No.: US 9,764,871 B2
(45) Date of Patent: Sep. 19, 2017

(54) AUTOMATIC BLOOD-SAMPLING TUBE PREPARATION DEVICE

(71) Applicant: TECHNO MEDICA CO., LTD., Yokohama-shi, Kanagawa (JP)

(72) Inventor: Mitsuru Sato, Sendai (JP)

(73) Assignee: TECHNO-MEDICA CO., LTD., Yokohama-shi (JP)

( * ) Notice: Subject to any disclaimer, the term of this patent is extended or adjusted under 35 U.S.C. 154(b) by 0 days.

(21) Appl. No.: 14/403,964

(22) PCT Filed: Jul. 17, 2013

(86) PCT No.: PCT/JP2013/069436
§ 371 (c)(1),
(2) Date: Nov. 25, 2014

(87) PCT Pub. No.: WO2015/008355
PCT Pub. Date: Jan. 22, 2015

(65) Prior Publication Data
US 2016/0152367 A1 Jun. 2, 2016

(51) Int. Cl.
*B65C 3/12* (2006.01)
*B65C 9/18* (2006.01)
(Continued)

(52) U.S. Cl.
CPC ............ *B65C 3/12* (2013.01); *A61B 5/15003* (2013.01); *A61B 5/150786* (2013.01);
(Continued)

(58) Field of Classification Search
CPC .. B65C 3/02; B65C 3/065; B65C 3/08; B65C 3/12; B65C 3/16; B65C 3/163; B65C 9/1865
(Continued)

(56) References Cited

FOREIGN PATENT DOCUMENTS

| JP | 10-062428 A | 3/1998 |
|---|---|---|
| JP | 3070522 B2 | 7/2000 |

(Continued)

OTHER PUBLICATIONS

Translation: JP 2002-340910, Nov. 2002, Matsumoto, Shunichi.*

(Continued)

*Primary Examiner* — George Koch
(74) *Attorney, Agent, or Firm* — Stites & Harbison, PLLC; Jeffrey A. Haeberlin; James R. Hayne

(57) ABSTRACT

A blood-sampling-tube automatic preparation device comprising a blood-sampling-tube containing section having at least two blood-sampling-tube containers, a label printing and pasting unit that prints blood sampling information data and then pastes the printed label on a surface of a blood-sampling-tube, a hand pasting label printer, a blood-sampling-tube collecting section in which one or more blood-sampling-tubes with label pasted and/or one or more printed labels for hand pasting are collected for each patient, a blood-sampling-tube transferring device that receives a blood-sampling-tube from the blood-sampling-tube container and transfers it to the label printing and pasting unit, and a control device that controls each component. All blood-sampling-tube containers of the blood-sampling-tube containing section are arranged in a row on a same horizontal surface and the blood-sampling-tube transferring device, the label printing and pasting unit, and the hand pasting label printer are arranged to be mutually superposed under the blood-sampling-tube containing section.

3 Claims, 4 Drawing Sheets

(51) Int. Cl.
*A61B 5/15* (2006.01)
*G01N 35/04* (2006.01)
*A61B 5/154* (2006.01)
*G01N 35/00* (2006.01)

(52) U.S. Cl.
CPC ........... *B65C 9/1865* (2013.01); *G01N 35/04* (2013.01); *A61B 5/154* (2013.01); *G01N 2035/00861* (2013.01)

(58) Field of Classification Search
USPC .................. 156/361, 367, 378, 379, 387
See application file for complete search history.

(56) References Cited

FOREIGN PATENT DOCUMENTS

| JP | 2000-247315 A | 9/2000 |
|---|---|---|
| JP | 2002-191688 A | 7/2002 |
| JP | 2002-337829 A | 11/2002 |
| JP | 2002340910 A * | 11/2002 |
| JP | 2005-67660 A | 3/2005 |
| JP | 4356096 B1 | 11/2009 |
| JP | 2010-085289 A | 4/2010 |
| JP | 2013-139314 A | 7/2013 |
| JP | 2013-140060 A | 7/2013 |
| WO | 2014/010608 A1 | 1/2014 |

OTHER PUBLICATIONS

Translation: JP 2002-191688, Jul. 2002, Masaaki, Takeda.*
Translation: JP 2002-337829, Nov. 2002, Matsumoto, Shunichi.*
Definition of "Superpose" from Merriam Webster. From http://www.merriam-webster.com/dictionary/superpose (last downloaded Oct. 12, 2016).*
JPO, International Search Report issued in corresponding international application No. PCT/JP2013/069436, mailed Oct. 15, 2013.

* cited by examiner (a)  (c)
(b)  (d)

AUTOMATIC BLOOD-SAMPLING TUBE PREPARATION DEVICE

This application is a 371 of PCT/JP2013/069436.

TECHNICAL FIELD

This invention relates to an improvement of a blood-sampling-tube automatic preparation device in which one or more blood-sampling-tubes are automatically selected from blood-sampling-tube container that contains the intended kind of the blood-sampling-tubes, respectively, and a label with printed blood-sampling information data related to a patient corresponding to the selected tubes is automatically pasted on each of the selected tubes, and then the tubes with the label pasted for every patients are contained.

BACKGROUND OF THE ART

In the operation of testing a blood-sample, the sample of one patient is typically examined for a number of test items. Therefore, in the hospital, the kinds of the blood-sampling-tubes are changed depending on the test items, and a worker writes the full name of the patients or the like on labels and pastes each of the labels on the blood-sampling-tubes in order to identify the test items and the patient name corresponding to the blood-sampling-tube at the blood test.

However, above mentioned works are very complicated since a worker writes the name of the patient on the label and pastes it on the each of the blood-sampling-tubes. In addition, if a human carries out these works, a serious mistake that the label is to be erroneously pasted on the unintended blood-sampling-tube or the like may occur.

In order to the above problems, an applicant of the present application has previously suggested a blood-sampling-tube automatic preparation device. In this device, at least two kinds of blood-sampling-tubes are contained in blood-sampling-tube containers according to the kinds of the blood-sampling-tubes, respectively. And one or more blood-sampling-tubes are selected and taken out from the corresponding blood-sampling-tube container. And blood-sampling information data related to the patient corresponding to the blood-sampling-tube(s) taken out from the blood-sampling-tube containers are printed on one or more label. And then each of the labels is pasted on the blood-sampling-tubes, respectively. And finally, one or more label pasted tubes for every patient are collected.

After the applicant suggested the above mentioned device, the applicant and the third parties in various ways have improved the blood-sampling-tube automatic preparation device, and improved devices have been proposed (Patent Documents 1 and 2).

Most of conventional blood-sampling-tube automatic preparation devices are constituted such that the blood-sampling-tube containers are arranged to be mutually superposed and thus the height of the device is high and a size of the device is big.

PRIOR ART DOCUMENT

Patent Documents

[Patent document 1] Japanese Patent No. 3070522.
[Patent document 2] Japanese Patent Kokai No. 2005-67660
[Patent document 3] Japanese Patent Application No. 2011-290475 (Japanese Patent Kokai No. 2013-140060)
[Patent document 4] Japanese Patent Application No. 2011-290295 (Japanese Patent Kokai No. 2013-139314)
[Patent document 5] PCT/JP2013/68787

SUMMARY OF THE INVENTION

Problems to be Solved by the Invention

An inventor of the present application invented a blood-sampling-tube automatic preparation device that is compact, may be set on a table and used on it. In the preparation device, pluralities of the blood-sampling-tube containers are longitudinally and/or laterally arranged on a same plane, not to be mutually superposed. In addition with the preparation device, a transferring device that transfers the blood-sampling-tube taken out from the corresponding blood-sampling-tube container to a label printing and pasting unit, under the blood-sampling-tube containers (Patent Documents 3 and 4).

And then the inventor suggested a blood-sampling-tube automatic preparation device that is more compact. In the preparation device, pluralities of the blood-sampling-tube containers are longitudinally and/or laterally arranged on a same plane and a label printing and pasting unit is arranged under the blood-sampling-tube containers (Patent Document 5).

There is provided a blood-sampling-tube automatic preparation device according to the present invention, as a result of intensive research, having a quit short width and very compact, in which one or more different kinds of blood-sampling-tubes with the label pasted may be certainly prepared according to an order of the Doctor. And the device has superior portability so that it becomes available in a small hospital, a ward for inpatients and a blood sampling center or the like. Furthermore, the device has superior emergency response in time of disaster or the like, because the device may be set on a desktop and used on it, may be used at a bed side, or may be set on a movable carrier and used on it.

It is an object of the present invention to provide above blood-sampling-tube automatic preparation device.

Means for Solving the Problems

To achieve the above object, the blood-sampling-tube automatic preparation device according to the present invention, comprising a blood-sampling-tube containing section having at least two blood-sampling-tube containers each of which are able to contain separately blood-sampling-tubes according to a kind of blood-sampling-tube, a label printing and pasting unit that prints a blood sampling information data related to a patient on a label and then pastes the printed label on a surface of a blood-sampling-tube, a hand pasting label printer, a blood-sampling-tube collecting section in which one or more blood-sampling-tubes with label pasted and, if necessary, one or more printed labels for hand pasting are collected for each patient, a blood-sampling-tube transferring device that receives the blood-sampling-tube required to a blood test of a patient from the corresponding blood-sampling-tube container and transfers the received blood-sampling-tube to the label printing and pasting unit, and a control device that controls the each component such as one or more blood-sampling-tubes required to the blood test of the patient are selectively taken out from the corresponding blood-sampling-tube container, the information data corresponding to the patient is printed on the label, the printed label is pasted each blood-sampling-tube, if necessary, the information data corresponding to the patient is printed on the label for hand pasting, and then one or more the label pasted blood-sampling-tubes and, if necessary, one or more labels for hand pasting are collected in the blood-sampling-tube collecting section for each patient characterized in that all blood-sampling-tube containers of the blood-sampling-tube containing section are arranged side by side in a row on a same horizontal surface and the blood-sampling-tube transferring device, the label printing and pasting unit, and the hand pasting label printer are arranged to be mutually superposed under the blood-sampling-tube containing section.

It is preferable that the blood-sampling-tube transferring device may comprise a first transferring device extending along the respective blood-sampling-tube container under thereof, the label painting and pasting unit may be arranged under the first transferring device, and the hand pasting label printer may be arranged under the label printing and pasting unit.

Furthermore it is preferable that the blood-sampling-tube transferring device may comprise a second transferring device that receives the blood-sampling-tube at one end of the first transferring device and transfers the received blood-sampling-tube to the label printing and pasting unit.

Effects of the Invention

The blood-sampling-tube automatic preparation device according to the present invention, comprising a blood-sampling-tube containing section having at least two blood-sampling-tube containers each of which are able to contain separately blood-sampling-tubes according to a kind of blood-sampling-tube, a label printing and pasting unit that prints a blood sampling information data related to a patient on a label and then pastes the printed label on a surface of a blood-sampling-tube, a hand pasting label printer, a blood-sampling-tube collecting section in which one or more blood-sampling-tubes with label pasted and, if necessary, one or more printed labels for hand pasting are collected for each patient, a blood-sampling-tube transferring device that receives the blood-sampling-tube required to a blood test of a patient from the corresponding blood-sampling-tube container and transfers the received blood-sampling-tube to the label printing and pasting unit, and a control device that controls the each component such as one or more blood-sampling-tubes required to the blood test of the patient are selectively taken out from the corresponding blood-sampling-tube container, the information data corresponding to the patient is printed on the label, the printed label is pasted each blood-sampling-tube, if necessary, the information data corresponding to the patient is printed on the label for hand pasting, and then one or more the label pasted blood-sampling-tubes and, if necessary, one or more labels for hand pasting are collected in the blood-sampling-tube collecting section for each patient characterized in that all blood-sampling-tube containers of the blood-sampling-tube containing section are arranged side by side in a row on a same horizontal surface and the blood-sampling-tube transferring device, the label printing and pasting unit, and the hand pasting label printer are arranged to be mutually superposed under the blood-sampling-tube containing section. As described above, since all components are arranged completely under the containers and the containers are arranged side by side in a row, a height, a width and a depth of the automatic preparation device are minimized.

Therefore the automatic preparation device according to the present invention may be set on a desk and used on it. Also the automatic preparation device according to the present invention may be set on a movable carrier and used on it. And the automatic preparation device according to the present invention may be used at the bed side in a ward for inpatients. Furthermore the automatic preparation device according to the present invention may be used at various scale facilities and various scenes.

MODE FOR CARRYING OUT THE INVENTION

An embodiment of a blood-sampling-tube automatic preparation device according to the present invention will be explained with reference to an example disclosed in attached drawings.

First, the layout of components which constitute the blood-sampling-tube automatic preparation device will be explained with reference to FIGS. 1 to 3.

Figure 1:
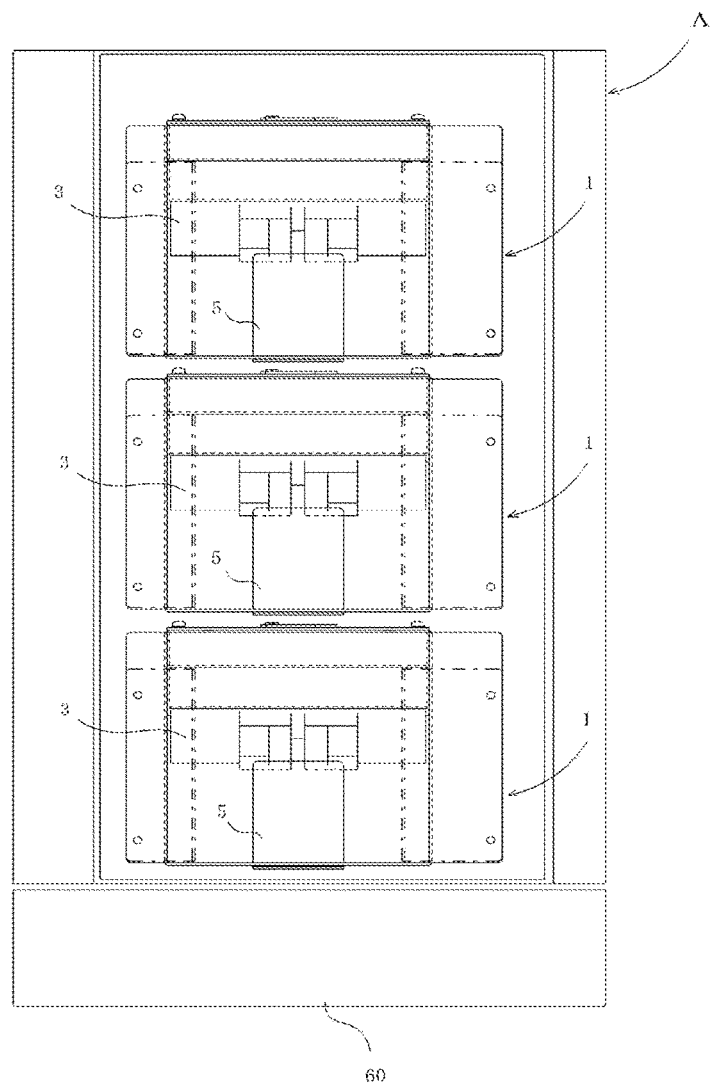
FIG. 1 is a schematic top view of the blood-sampling-tube automatic preparation device according to the present invention.
Figure 3:
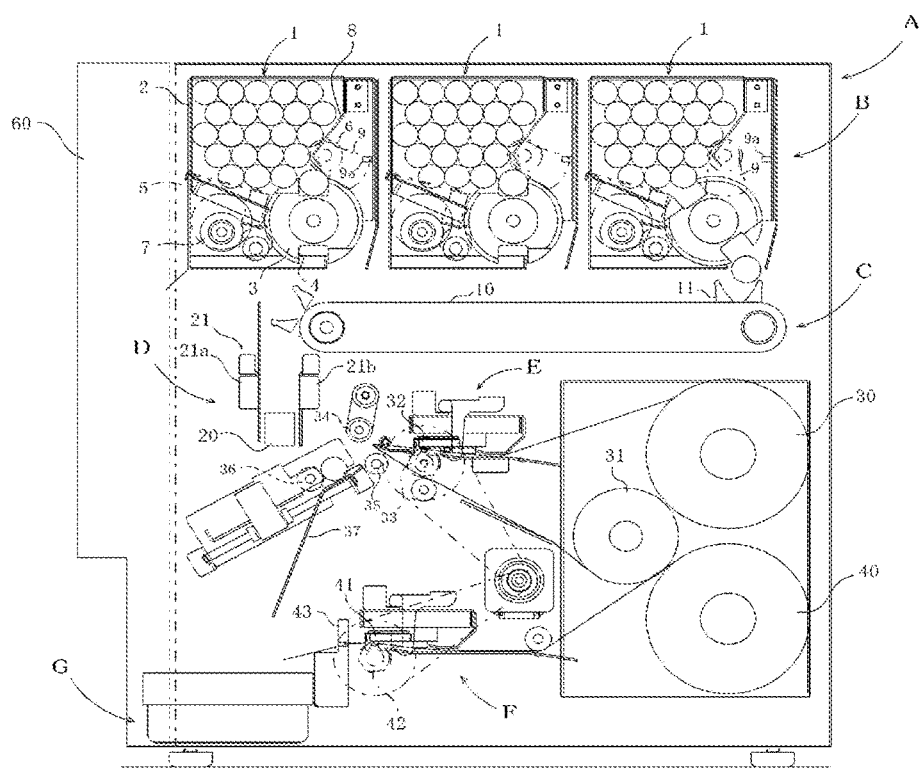
FIG. 3 is a schematic view showing an internal structure of the preparation device shown in FIG. 1, looked at from the right side of the preparation device.

As shown in FIGS. 1 and 3, this blood-sampling-tube automatic preparation device A comprises a blood-sampling-tube containing unit B in which three blood-sampling-tube containers 1 are parallel arranged in a longitudinal direction on a same plane. A first transferring device C is arranged to extend along the respective containers 1 of the blood-sampling tube containing unit B under thereof as shown in FIG. 3.

The transferring device C comprises a conveyor 10 having at least one bucket 11. The conveyor 10 which constitutes the first transferring device C receives a blood-sampling-tube taken out from each blood-sampling-tube container 1 with said bucket 11, and transfers it to a second transferring device D that is positioned downstream of the first transferring device C.

That is, the second transferring device D is arranged under one end (left end in FIG. 3) of the conveyor 10 of the first transferring C.

The second transferring device D is arranged under the blood-sampling-tube container 1 that is positioned at the most front side (most left side in FIG. 3) of the blood-sampling-tube containing unit B. And the second transferring device D comprises a conveyor 20 extending in a direction perpendicular to the conveyor 10. When the bucket 11 provided on the conveyor 10 turns at the downstream end of the conveyor 10, the blood-sampling-tube in the bucket 11 falls on the conveyor 20 under the function of gravity and thus is received by the conveyor 20 (See the FIG. 4(a)).

The second transferring device D comprises a blood-sampling-tube transfer means 21 for pushing out the blood-sampling-tube on the conveyor 20 to a label printing and pasting unit E.

The label printing and pasting unit E and a hand pasting label printer F are arranged to be mutually superposed under the unit B. The label printing and pasting unit E prints blood-sampling information related to a patient on one or more label and pastes them on the corresponding blood-sampling-tube(s). On the lower position of a space in front of the device E and the printer F, a blood-sampling-tube collecting section G is disposed. In this embodiment said section G is consist of a section for receiving a tray for collecting at least one blood-sampling-tube. One or more blood-sampling-tubes with the labels each on which the blood-sampling information data related to the patient is printed are collected into a tray on the section G for each patient. A sensor (not shown) for detecting the existence of a tray is arranged in the tray receiving section G.

Switches and a monitor (not shown in figures) displaying the state of each parts of the blood-sampling-tube automatic preparation device are arranged in an upper part of a front door 60 provided on a front side of the automatic preparation device.

The automatic preparation device has a control device 70. The control device 70 receives a blood sampling directive information data related to the patient from a host computer and controls an operation of each component of the automatic preparation device on the basis of the received directive information data.

In the blood-sampling-tube automatic preparation device A constituted as described above, the blood-sampling-tube containing unit B, the first and second transferring device C and D, the label printing and pasting unit E, the hand pasting label printer F and the tray receiving section G are arranged to be mutually superposed. And also in the device A, all of the first and second transferring device C and D, the label printing and pasting unit E, the hand pasting label printer F, and the tray receiving section G are positioned just under the unit B.

Lateral and longitudinal dimensions of the whole automatic preparation device A depend on lateral and longitudinal dimensions of the unit B as shown in the top view of the device A of FIG. 1 since the other components C to G are positioned just under the unit B, that is the lateral and longitudinal dimensions of the device A are minimized. So the blood-sampling-tube automatic preparation device A may be put in a small hospital, an in-patients ward, or a special facility for blood sampling, which have a restriction in space. Also the device A may be used at a side of a hospital bed. Furthermore the device may be set on a desk and used on it. And, the device A may be used by mounting it on a movable carrier, so that the device A has superior emergency response in time of disaster or the like.

Each component which constitutes the blood-sampling-tube automatic preparation device A will be explained respectively.

At First, the blood-sampling-tube containers 1 will be explained below.

Figure 2:
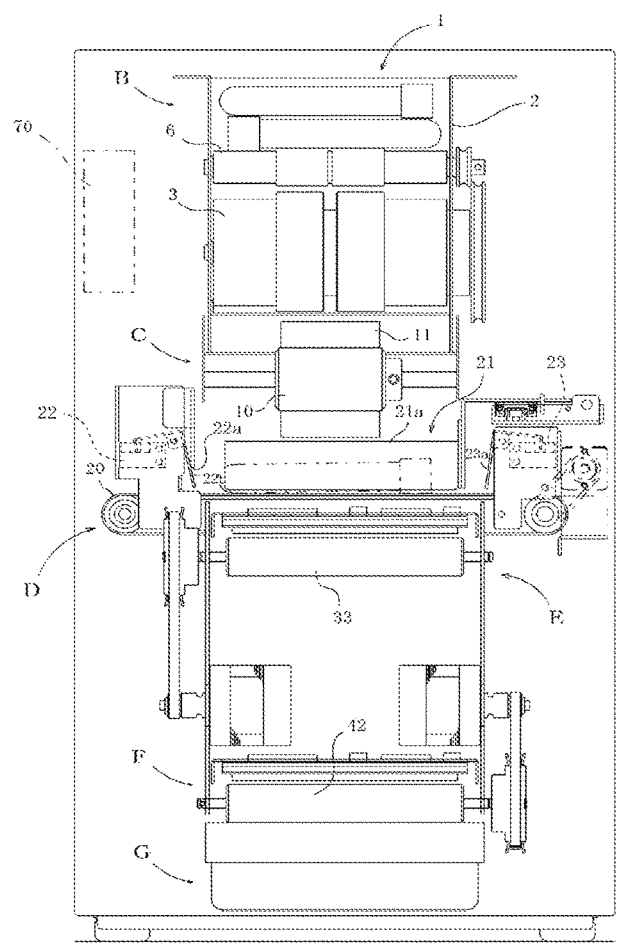
FIG. 2 is a schematic view showing an internal structure of the preparation device shown in FIG. 1, looked at from the front of the preparation device.

As shown in FIGS. 1 to 3, in this embodiment, each of blood-sampling-tube containers 1 comprises a rectangle body 2 made of thin metal plates, such as stainless steel plates, aluminum alloy plates, or steel plate. The rectangle body 2 has an upper opening and a lower opening. The upper opening is used as an entrance of the blood-sampling-tubes and a taking out roller 3 is arranged at one side of the lower opening. On an outer surface of the roller 3, two elongate grooves 4 for receiving the blood-sampling-tube are formed. They are arranged at opposite position. An inclination lower plate 5 which may be oscillated upward and downward is arranged at the other side of the lower opening. In the body 2, the blood-sampling-tubes are to be moved toward the taking out roller 3 by the function of the inclination lower plate 5, so that each the blood-sampling-tube is to be easily entered into the intended groove 4 of the roller 3.

A small auxiliary roller 6 is arranged above the roller 3. In case that each blood-sampling-tube contained in the blood-sampling-tube container 1 has a rubber cap, the rubber caps of the blood-sampling-tubes may contact with each other so that sometimes a problem may occur. For example, if the cap of the tube that is in the groove 4 contacts with the cap of the tube that is outside of the groove 4, a rotation of the roller 3 may be blocked by friction between the rubber caps. The auxiliary roller 6 is rotated to the opposite direction of the rotation direction of the roller 3 to push the tube being outside of the groove 4 contacted with the tube in the groove 4 in the opposite direction of the rotation direction of the roller 3, so that the tube being outside of the groove 4 separates from the tube in the groove 4. As a result, the auxiliary roller 6 ensures that the tube contained in the groove 4 may be only taken out.

A motor 7 is arranged in a space defined under the inclination plate 5 to move the taking out roller 3 and the auxiliary roller 6 and oscillate the plate 5 upwardly and downwardly.

A curved guide plate 8 is arranged above the auxiliary roller 6 so as to easily enter the blood-sampling-tube into the groove 4 as the blood-sampling-tube applied into the body 2 of the container 1 approaches the roller 3.

An attachment 9 for detecting whether the tube is in the groove 4 or not, and a sensor 9a for sensing and detecting the movement of the attachment 9 are arranged above the roller 3. The attachment 9 is rotatably mounted on an axis (with no numeral). Normally the attachment 9 droops under its own weight as shown in the most right side blood-sampling-tube container 1 in FIG. 3 and in this state the sensor 9a is turned off. From above state, the blood-sampling-tubes are moved toward the roller 3 by oscillating the plate 5 upwardly and downwardly while the roller 3 is rotated in a clockwise direction. When no blood-sampling-tube is in groove 4, even if the roller 3 is rotated, the attachment 9 is not moved. However, when the blood-sampling-tube is in the groove 4, if the roller 3 is rotated, the tube in the groove 4 is contacted with the attachment 9 and then the attachment 9 is moved in a counter-clockwise direction by the tube so that the sensor 9a turns on by the attachment 9. Thereby, the control device 70 detects that the blood-sampling-tube is in the groove 4 of the roller 3 and stops the roller 3 until the control device 70 receives a directive data which take out the tube from the groove 4 (See the most left side blood-sampling-tube container 1 and the center one in FIG. 3).

The conveyor 10 that constitutes the first transferring device C arranged under the blood-sampling-tube containing unit B comprises at least one bucket 11. The bucket 11 receives the blood-sampling-tube from the roller 3 of the each blood-sampling-tube container 1 and then the tube received in the bucket 11 is transferred to the second transferring device D that is positioned downstream of the first transferring device C. The bucket 11 is fixed on the conveyor 10 and when the bucket 11 turns at the downstream end of the conveyor 10, the blood-sampling-tube in the bucket 11 falls on the conveyor 20.

In this embodiment, the second transferring device D comprises the conveyor 20. A direction detecting means 22 is provided on one end of the conveyor 20 (right end of the conveyor 20 in FIG. 2) and a tube arrival detecting means 23 is provided in the other end of the conveyor 20 (left end of the conveyor 20 in FIG. 2).

The direction detecting means 22 comprises a switch 22b made of a U-shaped plate as shown in FIG. 2. The switch 22b is rotatably supported on an axis positioned at a corner of the switch. The switch 22b is normally waited with an inclined posture as shown in FIG. 2 so that one end of the switch 22b interrupts an irradiation light of the direction detecting means 22 to turn off it. The switch 22b is arranged behind an opening 22a having a size which a cap part of the blood-sampling-tube cannot pass through, although a bottom part of it can pass through. Therefore, the switch 22b may be pushed by the only bottom part of the blood-sampling-tube so that the direction of the tube may be detected.

The tube arrival detecting means 23 is arranged on the other end of the conveyor 20. The detecting means 23 comprises a switch 23a made of a U-shaped plate which can be pushed with the blood-sampling-tube on the conveyor 20.

When the conveyor 20 of the second transferring device D is received the blood-sampling-tube from the first transferring device C, the conveyor 20 is rotated to the left to transfer the tube to the direction detecting means 22. If said blood-sampling-tube lies on the conveyor 20, of which the cap is directed to the right end of the conveyor 20 (the right side in FIG. 2), the bottom part of the tube passes through the opening 22a and pushes the switch 22b to stand the U-shaped plate of the switch 22b so that the one end of the plate is to be no longer an interruption of the irradiation light and the direction detecting means 22 turns on. On the contrary, if said blood-sampling-tube lies on the conveyor 20, of which the cap is directed to the left end of the conveyor 20 (the left side in FIG. 2), the cap of the tube cannot pass through the opening 22a so that the switch 22b is not to be pushed. Thereby, in the basis of whether switch 22b is pushed or not by the blood-sampling-tube that lies on the conveyor 20, the control device 70 judges the direction of the blood-sampling-tube on the conveyor 20 and determines a print direction of the label printing and pasting unit F according to the direction of the blood-sampling-tube.

After that, the conveyor 20 is rotated to the right direction and transfers the blood-sampling-tube toward the tube arrival detecting means 23. If the blood-sampling-tube pushes the switch 23b by the cap or bottom part thereof, the control device 70 detects the arrival of the blood-sampling-tube and stops the conveyor 20.

The blood-sampling-tube transfer means 21 is arranged at the right side of the conveyor 20 in which the blood-sampling-tube that pushes the switch 23 is stopped. The blood-sampling-tube transfer means 21 has a pair of plates 21a and 21b that are arranged on opposite sides of the conveyor 20 and extend along with the conveyor 20. The plate 21b positioned at a side in which the printing and pasting device E is positioned, extends from under the conveyor 20 to above the conveyor 20. The plate 21a positioned at the opposite side of the plate 21b extends upward from just above the conveyor 20. These plates 21a and 21b are connected with each other to move together. They are biased by a spring (not shown in Figurers) so as to keep them at both side of the conveyor 20. These plates 21a and 21b are pushed out in a direction perpendicularly with the conveyor 20 against the spring force by a cam (not shown in Figures) driven by a motor (not shown in Figure) and then they stop when the plate 21a passes through the conveyor 20 (refer to FIG. 4(b)). The blood-sampling-tube on the conveyor 20, which is detected by the tube arrival detecting means 23, is pushed out from the conveyor 20 and falls down by the movement of the plates 21a and 21b above mentioned.

The label printing and pasting unit E comprises a label supply roller 30 having a label roll that is made of a wound continuous release coated paper on which labels are arranged and a rolling-up roller 31 for rolling up the release coated paper as shown in FIG. 3. The release coated paper is pulled out from the supply roller 30. During the paper passes through between a print head 32 and a platen roller 33, the printed head 32 prints the predetermined blood-sampling information data related to the patient on the label. The release coated paper is fold at a sharp angle during it passes through a peeling plate (with no numeral number) so that the label being flexible and harder to break than the release coated paper may be released from the paper.

After the label is released from the release coated paper, the label goes straight to a label pasting position and then it is pasted onto a surface of the blood-sampling-tube at the label pasting position. And after the label is released from the release coated paper, the release coated paper is only wound on the rolling-up roller 31. The control device 70 receives the required blood-sampling directive information data related to the patient from the host computer or the like and makes the print head 32 print the blood-sampling information data on the label.

The label printing and pasting unit E comprises a label pasting roller 34, an auxiliary roller 35 and a pressurizing roller 36.

The pressurizing roller 36 is constituted so that it may be moved between the label pasting position in which the roller 36 supports the blood-sampling-tube with the label pasting roller 34 and the auxiliary roller 35, a blood-sampling-tube receiving position in which the roller 36 received the blood-sampling-tube pushed out from the conveyor 20 by the tube transfer means 21, and a blood-sampling-tube discharging position in which the blood-sampling-tube with the label pasted may be discharged.

Figure 4:
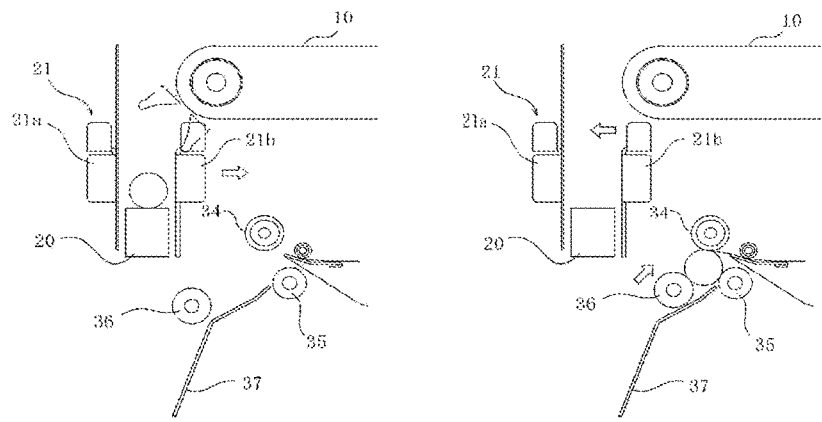
FIG. 4 (a) to (d) are partial views showing different phases of a function of the preparation device shown in FIG. 1.
Figure 4:
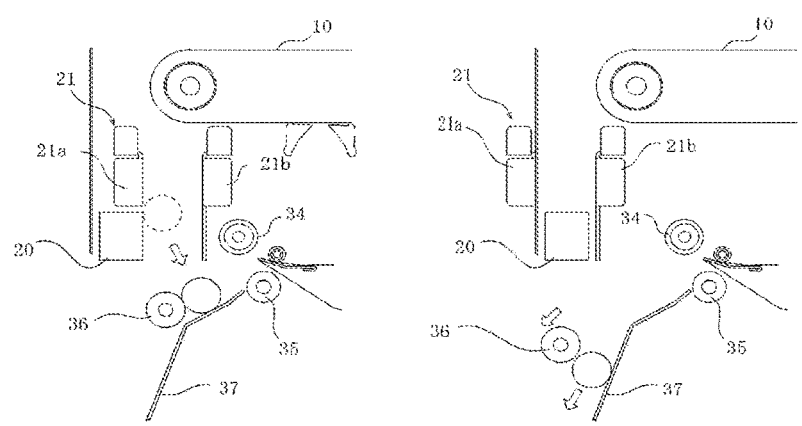

FIGS. 4 (a) and (b) show the state where the pressurizing roller 36 is positioned at the blood-sampling-tube receiving position, FIG. 4 (c) shows the state where the roller 36 is positioned at the label pasting position, and FIG. 4 (d) shows the state where the roller 36 is positioned at the blood-sampling-tube discharging position.

In FIG. 3 the pressurizing roller 36 receives the blood-sampling-tube at the blood-sampling-tube receiving position. The pressurizing roller 36 is upwardly moved from the blood-sampling-tube receiving position to the label pasting position in which the blood-sampling-tube is pushed against the label pasting roller 34 and the auxiliary roller 35 by the pressurizing roller 36. In the label pasting position, the blood-sampling-tube is supported at the three points by the label pasting roller 34, the auxiliary roller 35 and the pressurizing roller 36. The printed label that is released from the release coated paper enters between the blood-sampling-tube and the label pasting roller. And then the label is pasted on the surface of the blood-sampling-tube while the tube is rotated by the label pasting roller 34.

The pressurizing roller 36 is downwardly moved after the label is completely pasted on the tube. The pressurizing roller 36 is downwardly moved under the blood-sampling-tube receiving position with the blood-sampling-tube. As shown in FIG. 3, a supporting plate 37 that supports the blood-sampling-tube together with the pressurizing roller 36 is extended along the movement direction of the pressurizing roller 36 to the middle portion thereof and is downwardly bent toward the tray receiving section G from the middle portion thereof. Therefore, when the pressurizing roller 36 is moved to the lowest position (i.e. the blood-sampling-tube discharging position), the label pasted tube falls down along the supporting plate 37 and is received into a tray arranged on the tray receiving section G.

The hand pasting label printer F is arranged under the label printing and pasting unit E so that they are mutually superposed.

The hand pasting label printer F comprises a label supply roller 40, a print head 41 and a platen roller 42. The label supply roller 40 has a label roll that is made of a wound continuous release coated paper on which labels are arranged. The print head 41 prints a blood-sampling information data on a label on the basis of the blood-sampling directive information data related to the patient. The hand pasting label printer F also comprises a cutting device 43 to cut the release coated paper together with the printed label.

The cutting device 43 is arranged by the tray on the tray receiving section G so that the cut release coated paper with the printed label may fall into the tray.

The control device 70 receives the required blood-sampling directive information data related to the patient from the host computer or the like and makes the print head 41 print the blood-sampling information data on the label.

A front part of the tray receiving section G is opened so that a user may remove the tray from the section G and put it on the section G.

Finally, the function of the blood-sampling-tube automatic preparation device A described above will be explained. At first, the different kinds of the blood-sampling-tubes are thrown into the corresponding body 2 of the blood-sampling-tube containers 1 via an opening arranged in the upper surface thereof. Direction of the blood-sampling-tube in the container 1 may turn to any direction.

After the blood-sampling-tubes are contained in the corresponding blood-sampling-tube container, the device A is turned on so that the control device 70 also is turned on and receives a blood sampling directive information data related to the patient whose blood to be collected from the host computer etc.

The control device 70 judges the kind of blood-sampling-tube required to blood sampling related to the patient on the basis of the received blood-sampling directive information data and drives a driving motor mounted on the blood-sampling-tube container 1 containing the corresponding kind of blood-sampling-tubes so that the taking out roller 3 and the auxiliary roller 6 rotates in the clockwise direction in FIG. 3. During the rolls 3 and 6 are rotated, a blood-sampling-tube is dropped and contained in the groove 4 of the taking out roller 3.

And even if the cap of the blood-sampling-tube contained in the groove 4 contacts with the cap of the other blood-sampling-tube not contained in the groove 4, the blood-sampling-tube not contained in the groove 4 is pushed back with the auxiliary roller 6 so that the tube not contained in the groove 4 will be completely separated with the tube contained in the groove 4.

The attachment 9 and the sensor 9a detects whether the blood-sampling-tube is contained in the groove 4 or not, and the control device 70 keeps the state that blood-sampling-tube is contained in the groove 4 of the each blood sampling container 1 on the basis of the result of the detection of the sensor 9a.

The control device 70 rotates the taking out roller 3 of the blood-sampling-tube container 1 that contains the blood-sampling-tube required to the blood sampling in the clockwise direction on the basis of the blood sampling directive information data, so that the groove 4 is directed downward and the blood-sampling-tube in said groove 4 falls into the bucket 11 of the conveyor 10 arranged under the blood-sampling-tube container 1. And then the blood-sampling-tube contained in the bucket 11 is conveyed to the left side of FIG. 3 by the conveyor 10.

When the bucket 11 provided on the conveyor 10 turns at the downstream end of the conveyor 10, the blood-sampling-tube in the bucket 11 falls on the conveyor 20 arranged under the conveyor 10. The conveyor 20 receives it (See the FIG. 4(a)).

At first the conveyor 20 transfers the blood-sampling-tube supplied by the first transferring device C to the left side in the FIG. 2 so that the direction of the blood-sampling-tube is detected by the direction detecting means 22. And then the conveyor 20 transfers the blood-sampling-tube to the right side in FIG. 2 so that the blood-sampling-tube pushes the switch 23a of the tube arrival detecting means 23.

At this time, the pressurizing roller 36 of the label printing and pasting unit E is positioned at the blood-sampling-tube receiving position (See the FIG. 4 (a)).

When the blood-sampling-tube arrival detecting means 23 detects the blood-sampling-tube, the blood-sampling-tube transfer means 21 moves the plates 21a and 21b in the direction orthogonally with the moving direction of the conveyor 20 by the cam. Whereby the plate 21a pushes out the blood-sampling-tube from the conveyor 20 so that the tube falls on the pressurizing roller 36 positioned at the blood-sampling-tube receiving position (See FIG. 4(b)).

When the blood-sampling-tube is arrived at the blood-sampling-tube receiving position, the pressurizing roller 36 is moved upwardly to transfer the blood-sampling-tube to the label pasting position and the blood-sampling-tube is to be supported at the three points by the rollers 34, 35 and 36 at the label pasting position (See FIG. 4(c)).

During above process, the control device 70 makes the print head 32 print the blood sampling information data related to the patient corresponding to the blood-sampling-tube on the label. The direction of the printing is determined on the basis of the direction of the blood-sampling-tube detected by the direction detecting means 22. The printed label is sent between the blood-sampling-tube and the label pasting roller 34 at the label pasting position. Thereby, while rotating the blood-sampling-tube with the three rollers 34, 35 and 36, the printed label is pasted on the surface of the blood-sampling-tube by the label pasting roller 34.

After the label is completely pasted on the blood-sampling-tube, the pressurizing roller 36 is moved downwardly. The pressurizing roller 36 is moved until under the blood-sampling-tube receiving position with the label pasted blood-sampling-tube. While the pressurizing roller 36 is moved downwardly to the blood-sampling-tube discharging position (See FIG. 4(d)), the blood-sampling-tube falls down along the supporting plate 37 and enters into the tray on the tray receiving section G.

If necessary, the control device 70 makes the print head 41 of the hand pasting label printer F print the blood sampling information data on a label for hand pasting and then cutting device 43 cuts the release coated paper with the printed label so that it falls into the tray.

The above-mentioned process is repeated until the all blood-sampling-tubes for one patient are contained in the tray and then the process is finished.

Whereby one or more the label pasted blood-sampling-tubes required to the blood sampling of the patient and, if necessary, one or more the hand pasting labels are contained in a tray for one patient.

The preparation device A may be constituted such as when the tray is changed to new one, the process for next patient is automatically started. Also the device A may be constituted such as when the tray is changed to new one and a start switch (not shown) is pushed, the process for next patient is started.

In the above mentioned embodiment, the first transferring device C and the second transferring device D are arranged under the blood-sampling-tube containing unit B. However the construction of the transferring device is not limited by this embodiment. The transferring device may be constituted such as the first transferring device C transfers the blood-sampling-tube directly to the label printing and pasting unit E.

Also in the above embodiment, the label printing and pasting unit E prints the information data in the form of the barcode on the label. However the above construction of the label printing and pasting unit E is not limited by this embodiment. For example, a label having a wireless tag may be used in the preparation device A and the blood sampling information data may be recorded in the wireless tag and also printed on the label.

DESCRIPTION OF THE REFERENCE NUMERAL

A blood sampling tube preparation device
B blood sampling tube containing unit
C first transferring device
D second transferring device
E label printing and pasting unit
F hand pasting label printer
G blood-sampling-tube collecting section
1 blood sampling tube container
2 body (rectangle body)
3 taking out roller
4 elongate grooves
5 inclination lower plate
6 small auxiliary roller
7 motor
8 guide plate
9 attachment
9a sensor
10 conveyor
11 bucket
20 conveyor
21 blood sampling tube transfer means
22 direction detecting means
22b switch 22b made of U-shaped plate
23 tube arrival detecting means
30 label supply roller
31 rolling-up roller
32 print head
33 plantain roller
34 label pasting roller
35 auxiliary roller
36 pressurizing roller
37 supporting plate
40 label supply roller
41 print head
42 platen roller
43 cutting device
60 front door
70 control device

The invention claimed is:

1. A blood-sampling-tube automatic preparation device comprising
a blood-sampling-tube containing section having at least two blood-sampling-tube containers each of which are able to contain separately blood-sampling-tubes according to a kind of blood-sampling-tube,
a label printing and pasting unit that prints a blood sampling information data related to a patient on a label and then pastes the printed label on a surface of a blood-sampling-tube,
a hand pasting label printer,
a blood-sampling-tube collecting section in which one or more blood-sampling-tubes with label pasted and, if necessary, one or more printed labels for hand pasting are collected for each patient,
a blood-sampling-tube transferring device that receives the blood-sampling-tube required to a blood test of a patient from the corresponding blood-sampling-tube container and transfers the received blood-sampling-tube to the label printing and pasting unit, and
a control device that controls the each component such as one or more blood-sampling-tubes required to the blood test of the patient are selectively taken out from the corresponding blood-sampling-tube container, the information data corresponding to the patient is printed on the label, the printed label is pasted each blood-sampling-tube, if necessary, the information data corresponding to the patient is printed on the label for hand pasting, and then one or more the label pasted blood-sampling-tubes and, if necessary, one or more labels for hand pasting are collected in the blood-sampling-tube collecting section for each patient
wherein
all blood-sampling-tube containers of the blood-sampling-tube containing section are arranged side by side in a row on a same horizontal surface,
the blood-sampling-tube transferring device, the label printing and pasting unit, and the hand pasting label printer are arranged to be mutually superposed under the blood-sampling-tube containing section such that neither the blood-sampling-tube transferring device, the label printing and pasting unit, nor the hand pasting label printer substantially extends past a width of the blood-sampling-tube container section taken orthogonal to a direction in which the at least two blood-sampling-tube containers are aligned,
the label printing and pasting unit is positioned under the blood-sampling-tube transferring device to downwardly transfer the blood-sampling-tube from the blood-sampling-tube transferring device to the label printing and pasting unit and to downwardly discharge a label pasted tube, and
the hand pasting label printer is positioned under the label printing and pasting unit to downwardly discharge a printed hand pasting label.

2. The blood-sampling-tube automatic preparation device as claimed in claim 1
wherein
the blood-sampling-tube transferring device comprises a first transferring device extending along the respective blood-sampling-tube container under thereof,
the label painting and pasting unit is arranged under the first transferring device, and
the hand pasting label printer is arranged under the label printing and pasting unit.

3. The blood-sampling-tube automatic preparation device as claimed in claim 2
wherein
the blood-sampling-tube transferring device comprises a second transferring device that receives the blood-sampling-tube at one end of the first transferring device and transfers the received blood-sampling-tube to the label printing and pasting unit.

* * * * *